United States Patent [19]

Murakami et al.

[11] Patent Number: 5,587,467
[45] Date of Patent: Dec. 24, 1996

[54] SEPARATING AGENT FOR OPTICAL ISOMERS AND PROCESS FOR PRODUCING THE SAME

[75] Inventors: Tatsushi Murakami; Akito Ichida, both of Hyogo, Japan

[73] Assignee: Daicel Chemical Industries, Ltd., Osaka, Japan

[21] Appl. No.: 374,530

[22] PCT Filed: Jun. 21, 1994

[86] PCT No.: PCT/JP94/00992

§ 371 Date: Jan. 11, 1995

§ 102(e) Date: Jan. 11, 1995

[87] PCT Pub. No.: WO95/00463

PCT Pub. Date: Jan. 5, 1995

[30] Foreign Application Priority Data

Jun. 22, 1993 [JP] Japan ................. 5-149956
Jun. 16, 1994 [JP] Japan ................. 6-134183
Jun. 20, 1994 [JP] Japan ................. 6-137214

[51] Int. Cl.$^6$ ............ C08B 3/12; C08B 3/30; C08B 15/10; C08B 31/04; B01J 20/10

[52] U.S. Cl. ............ 536/18.5; 436/527; 436/529; 502/404; 502/405; 536/56; 536/58; 536/63

[58] Field of Search ............ 536/18.6, 58, 56, 536/63, 62, 18.5; 423/339; 436/527, 529; 502/404, 405; 524/492, 493, 494

[56] References Cited

U.S. PATENT DOCUMENTS 4,040,022  5/1978  Tsao et al. ................. 536/57

FOREIGN PATENT DOCUMENTS 61-181960   8/1986   Japan.
63-250327  10/1988   Japan.
4-314710   11/1992   Japan.

OTHER PUBLICATIONS

J. Am. Chem. Soc., vol. 106, pp. 5357–5359, 1984.

*Primary Examiner*—Gary L. Kunz
*Attorney, Agent, or Firm*—Flynn, Thiel, Boutell & Tanis, P.C.

[57] ABSTRACT

Polysaccharide derivative molecules are crosslinked exclusively among themselves on a support such as silica gel with the use of a polyfunctional crosslinking agent to immobilize the polysaccharide derivative on the support. The separating agent for optical isomers produced by the method has a high solvent resistance and, therefore, is most suitable as a separating agent for optical resolution.

19 Claims, No Drawings

SEPARATING AGENT FOR OPTICAL ISOMERS AND PROCESS FOR PRODUCING THE SAME

FIELD OF THE INVENTION

The present invention relates to a separating agent for optical isomers and a process for producing the same. More particularly, it relates to a separating agent, which is obtained by crosslinking polysaccharide derivative molecules only among themselves on a support and useful as an optical resolution reagent for racemic modifications, and a process for producing the same.

DESCRIPTION OF RELATED ART

It is known that a column packing composed of silica gel having a polysaccharide derivative supported thereon is useful as a separating agent for optical isomers of a racemic modification (Y. Okamoto, M. Kawashima and K. Hatada, J. Am. Chem. Soc., 106, p.5357, 1984). However, such a separating agent is poor in solvent resistance since it comprises silica gel having a polysaccharide derivative which is supported on the silica gel simply by coating alone. When the separating agent is used as a column packing for liquid chromatography, therefore, some eluents cannot be used.

Accordingly, a separating agent which is composed of a support having a polysaccharide derivative supported thereon and has an excellent solvent resistance has been required.

SUMMARY OF THE INVENTION

The present inventors have conducted extensive studies on a separating agent whereby the above-mentioned problems can be solved without deterioration of the excellent characteristics of a polysaccharide derivative and, as a result, completed the present invention.

Thus, the present invention provides a separating agent for optical isomers which is characterized by being composed of a polysaccharide derivative which has been immobilized on a support through crosslinkage of polysaccharide derivative molecules only among themselves on the support, a process for producing the separating agent for optical isomers of the present invention which is characterized by crosslinking polysaccharide derivative molecules only among themselves on a support with the use of a polyfunctional crosslinking agent, a use of the separating agent for optical isomers of the present invention as a column packing for chromatography, and a process for separating a mixture of optical isomers which comprises separating the mixture of optical isomers from each other by using the separating agent for optical isomers according to the present invention.

DETAILED DESCRIPTION OF THE INVENTION

Although the polysaccharide in the present invention may be any of a synthetic polysaccharide, a natural polysaccharide and a modified natural polysaccharide without restriction, so long as it is optically active, those having a high regularity in the mode of binding are preferable. Examples of the polysaccharide include β-1,4-glucan (cellulose), α-1,4-glucan (amylose, amylopectin), α-1,6-glucan (dextran), β-1,6-glucan (bustulan), β-1,3-glucan (e.g., curdlan, schizophyllan, etc.), α-1,3-glucan, β-1,2-glucan (crown gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, β-1,4-N-acetylchitosan (chitin), pullulan, agarose and alginic acid. In addition thereto, starches containing amylose and the like are involved in the category of polysaccharides. Among them, those which can be easily obtained in a highly pure state, for example, cellulose, amylose, β-1,4-chitosan, chitin, β-1,4-mannan, β-1,4-xylan, inulin and curdlan, are preferable and cellulose and amylose are preferable in particular.

The number-average degree of polymerization (the average number of pyranose or furanose rings per molecule) of the polysaccharide is 5 or above, preferably 10 or above. Although the upper limit of the number-average degree of polymerization of the polysaccharide is not particularly defined, it is preferable that the number-average degree of polymerization thereof does not exceed 500 from the viewpoint of workability.

An example of the polysaccharide derivative to be used in the present invention is a compound which is obtained by reacting such a polysaccharide as those cited above with a compound having a functional group capable of reacting with a hydroxyl group of the polysaccharide by a publicly known method and in which some of the hydroxyl groups of the starting poly-saccharide form ester bonds or urethane bonds.

Examples of the compound having a functional group capable of reacting with a hydroxyl group include isocyanic acid derivatives, carboxylic acids, esters, acid halides, acid amides, halides, epoxides, aldehydes, alcohols and other compounds having leaving groups. They may be any of aliphatic compounds, alicyclic compounds, aromatic compounds and heteroaromatic compounds.

Particularly preferable polysaccharide derivatives to be subjected to the crosslinkage in the present invention are esters or carbamate derivatives of cellulose or amylose having at least 0.1 unreacted hydroxyl group per glucose unit, compounds having at least 0.1 reactive, functional group per glucose unit in the groups introduced into cellulose or amylose so as to convert it into the ester or carbamate derivative thereof, and the like. As examples of the reactive functional group, hydroxyl group, amino group, mercapto group, carboxyl group and vinyl group may be cited.

Examples of the support to be used in the present invention include porous organic supports and porous inorganic supports having surface which have been inactivated to thereby prevent them from reacting with a crosslinking agent, and porous inorganic supports are preferable. Appropriate porous organic supports include those composed of polymers such as polystyrene, polyacrylamide and polyacrylate. Appropriate porous inorganic supports include silica gel, silica, alumina, magnesia, glass, kaolin, titanium oxide, silicates and the like. As a particularly preferable support, silica gel may be cited. The particle size thereof ranges from 1 μm to 10 mm, preferably from 1 to 1,000 μm and still more preferably from 1 to 300 μm, while the average pore size thereof ranges from 10 Å to 100 μm, preferably from 50 to 50,000 Å. The treatment for inactivating the surface of silica gel can be effected by a publicly known method.

Examples of the polyfunctional crosslinking agent to be used in the present invention in order to crosslink polysaccharide derivative molecules exclusively among themselves include polyfunctional isocyanate derivatives, acid chloride derivatives of dicarboxylic acids, diepoxy derivatives and divinyl derivatives. These crosslinking agents may be any of aliphatic compounds and aromatic compounds. As the polyfunctional crosslinking agent, diisocyanate derivatives are preferable in particular.

In the present invention, the one composed of a crosslinked polysaccharide derivative which is obtained by selectively crosslinking the hydroxyl groups at the 6-position of cellulose or amylose with each other is particularly preferable.

The crosslinking ratio of the polysaccharide derivative preferably ranges from 1 to 20%. The term "crosslinking ratio" as used herein means the ratio of the unreacted hydroxyl groups and/or reactive functional groups participating in the crosslinkage to all the hydroxyl groups of the starting poly-saccharide., supposing that the unreacted hydroxyl groups or reactive functional groups in the polysaccharide derivative react with the functional groups of the polyfunctional crosslinking agent at a ratio of 1:1.

To crosslink either the hydroxyl groups in the polysaccharide derivative with each other, the reactive functional groups therein with each other or the hydroxyl groups with the reactive functional groups therein, the polysaccharide derivative must be supported (immobilized) on a support having surfaces which has been previously subjected to an inactivation treatment. An example of the method for immobilization is coating of the support with a solution of the polysaccharide derivative. The amount of the polysaccharide derivative to be immobilized on the support ranges preferably from 1 to 100% by weight, still more preferably from 5 to 60% by weight, based on the weight of the support.

Now an example of the process for producing the separating agent of the present invention will be described.

Cellulose is reacted with trityl chloride to thereby give 6-0-tritylcellulose. The tritylcellulose thus obtained is reacted with a compound which has a functional group capable of reacting with a hydroxyl group by a publicly known method. Thus, the hydroxy groups in the tritylcellulose form ester bonds or urethane bonds together with the functional groups of the compound having the functional group capable of reacting with a hydroxyl group. The cellulose derivative thus obtained is treated with an acid such as hydrochloric acid to thereby eliminate its trityl groups. Thus, a cellulose derivative according to the present invention is obtained. The obtained cellulose derivative according to the present invention is then dissolved in a solvent. Silica gel having a surface which has been inactivated is coated with the obtained solution to thereby give a silica gel coated with the cellulose derivative. The cellulose derivative of the cellulose-derivative-coated silica gel is reacted with a polyfunctional isocyanate derivative in a dry, inert solvent to thereby crosslink the cellulose derivative molecules among themselves. Thus, the separating agent according to the present invention wherein a cellulose derivative is immobilized on silica gel can be obtained.

The methods for immobilizing a polysaccharide derivative on a support by crosslinking the polysaccharide derivative molecules only among themselves on the support in the present invention include a method wherein the crosslinkage is effected in the hydroxyl group moiety originating in the starting polysaccharide of the polysaccharide derivative and another method wherein the crosslinkage is effected in the reactive functional group moiety carried by the groups which have been introduced into the polysaccharide in the step of the conversion of the polysaccharide into its derivative. The former includes the methods represented by the following reaction scheme.

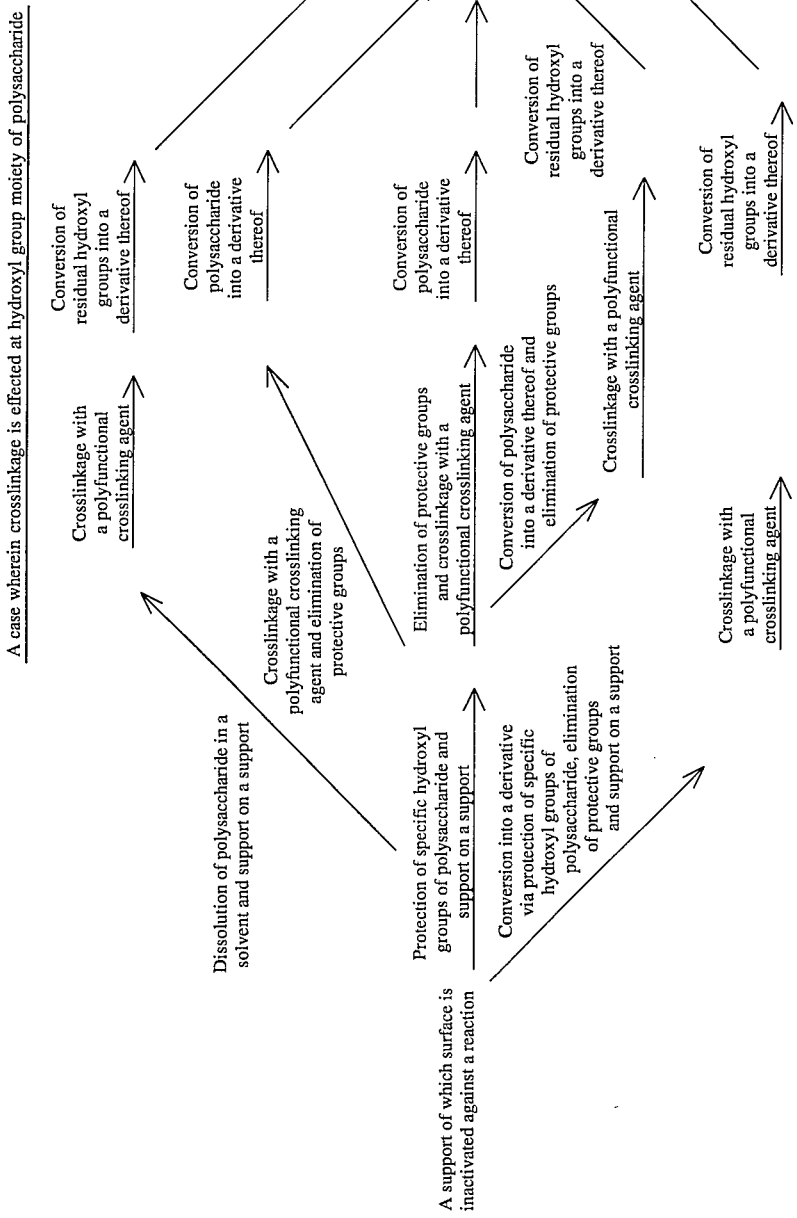

When the crosslinkage is effected at the reactive functional group moiety carried by the groups which have been introduced into the polysaccharide in the step of converting the polysaccharide into its derivative, a step of introducing a substituent carrying the reactive functional group may be added to each of the processes represented by the above-mentioned reaction scheme. Namely, when the polysaccharide is converted into the derivative prior to the crosslinkage, a compound having a functional group capable of reacting with a hydroxyl group together with another reactive functional group may be reacted with the polysaccharide or the polysaccharide derivative wherein specific hydroxyl groups are protected.

In the separating agent of the present invention obtained by such a method, a crosslinked polysaccharide derivative which is obtained by crosslinking polysaccharide derivative molecules among themselves with the use of a polyfunctional crosslinking agent includes a support therein to form such a structure that the support would not be released from the crosslinked polysaccharide derivative.

The separating agent for optical isomers according to the present invention is generally used in chromatographies such as gas chromatography, liquid chromatography and thin layer chromatography. Application thereof to liquid chromatography is particularly preferable. Thus, the separating agent for optical isomers according to the present invention is used as a column packing in various chromatographies.

Use of the separating agent for optical isomers of the present invention makes it possible to separate a mixture of optical isomers from each other.

The separating agent of the present invention has an excellent solvent resistance and, therefore, is most suitable as a separating agent for optical resolution.

EXAMPLES

The present invention will be hereinafter described in detail with reference to the Examples, though the present invention is not limited to these Examples only.

EXAMPLE 1

① Surface inactivation treatment of silica gel

Porous silica gel (Daiso SP-1000) was subjected to aminopropylsilane treatment (APS treatment) by a publicly known method. In 1,000 ml of methylene chloride, 200 g of the APS-silica gel thus obtained was reacted with 15 ml of 3,5-dimethylphenyl isocyanate at room temperature for 1.5 hours. The obtained product was separated by filtration with a glass filter, washed successively with a mixture of methylene chloride with methanol (2/1), methylene chloride, ethanol, acetone and n-hexane, and dried. Thus, silica gel having a surface which had been subjected to inactivation treatment was obtained.

② Synthesis of cellulose derivative
(6-hydroxy-2,3-bis (3,5-dimethylphenylcarbamate) derivative of cellulose)

Under a nitrogen atmosphere, 4.0 g of tritylcellulose having about 0.9 to 1 trityl group per glucose unit was dissolved in dry pyridine. To the solution thus obtained was added 10 ml of 3,5-dimethylphenyl isocyanate. Under a nitrogen atmosphere, the resulting mixture was stirred at 100° C. for 25 hours under heating. The reaction mixture thus obtained was poured into 700 ml of methanol. The solid thus precipitated was separated by filtration with a glass filter, washed successively with ethanol and n-hexane, and dried. Next, this solid was introduced into methanol containing conc. hydrochloric acid. The mixture thus obtained was stirred to thereby eliminate trityl groups from the reaction product. The solid was separated by filtration with a glass filter, washed successively with ethanol and n-hexane, and dried. Thus a 6-hydroxy-2,3-bis(3,5-dimethylphenylcarbamate) derivative of cellulose was obtained.

③ Preparation of silica gel supporting a cellulose derivative thereon 1.5 g of the cellulose derivative obtained in the above ② was dissolved in tetrahydrofuran. The resulting solution was uniformly poured onto 5.7 g of the silica gel obtained in the above ① and the solvent was volatilized to thereby support the cellulose derivative on the silica gel. The product thus obtained was washed successively with methanol, ethanol and n-hexane, and dried. Thus silica gel supporting the cellulose derivative thereon was obtained.

④ Immobilization of cellulose derivative on silica gel through crosslinkage exclusively among cellulose derivative molecules To 6.7 g of the silica gel supporting the cellulose derivative thereon obtained in the above ③ was added 35 ml of toluene which had been dried over metallic sodium (hereinafter referred to dry toluene). Further, 110 mg of diphenylmethane diisocyanate was added thereto. The mixture thus obtained was stirred at 110° C. for 6 hours under heating. After the completion of the reaction, the product was separated by filtration with a glass filter, washed successively with tetrahydrofuran, methanol, ethanol and n-hexane, and then dried. Thus, a separating agent composed of the cellulose derivative immobilized on the silica gel was obtained.

⑤ Modification of unreacted hydroxyl group in cellulose derivative immobilized on silica To the separating agent obtained in the above ④ were added 25 ml of dry toluene and 15 ml of dry pyridine. Further, 0.5 ml of 3,5-dimethylphenyl isocyanate was added thereto. The resulting mixture was stirred at 110° C. for 15 hours under heating. After the completion of the reaction, the product was separated by filtration with a glass filter, washed successively with tetrahydrofuran, methanol, ethanol and n-hexane, and dried. Thus,the unreacted hydroxyl groups in the cellulose derivative immobilized on the silica gel were carbamoylated.

The amount of the cellulose derivative supported on the silica gel was about 19% (calculated by supposing that the cellulose derivative, in which 2.5 hydroxyl groups, among 3, contained in the glucose unit of cellulose had been carbamoylated, was supported on the silica gel).

COMPARATIVE EXAMPLE 1

Preparation of separating agent composed of polysaccharide derivative immobilized on silica gel through crosslinkage of both polysaccharide derivative molecules among themselves and polysaccharide derivative with silica gel 1.8 g of tritylcellulose having about 0.9 to 1 trityl group per glucose unit was dissolved in tetrahydrofuran. The solution thus obtained was uniformly poured onto 6.0 g of aminopropylsilane-treated silica gel (mfd. by Daiso Co., Ltd.). The solvent was volatilized and thus the tritylcellulose was supported on the silica gel. Onto this silica gel were poured 75 ml of methanol and 0.75 ml of conc. hydrochloric acid. The obtained mixture was allowed to stand at room temperature overnight to thereby eliminate trityl groups from the cellulose. The product was separated by filtration and washed with methanol. 75 ml of methanol and 0.75 ml of triethylamine were poured thereonto and the resulting mixture was stirred for 5 minutes. The product was separated by filtration, washed with methanol, and then dried.

Under a nitrogen atmosphere, a mixture obtained by dissolving 49.3 mg of 4,4'-diphenylmethane diisoeyanate in 6.5 ml of dry toluene was added to 3.4 g of the silica gel having cellulose adsorbed thereon as obtained above. Further, 2.5 ml of dry pyridine was added thereto. The mixture thus obtained was stirred at 60° C. under heating. After 5 hours, 20 ml of dry pyridine and 0.75 ml of 3,5-dimethylphenyl isoeyanate were added thereto, followed by heating to 110° C. After 18 hours, the reaction mixture thus obtained was filtered through a glass filter and the precipitate thus obtained was washed with tetrahydrofuran. The precipitate was washed successively with methanol, ethanol and n-hexane before drying, and then dried. Thus was obtained a separating agent composed of the polysaccharide derivative immobilized on the silica gel through crosslinkage of both of the polysaccharide derivative molecules among themselves and the polysaccharide derivative with the silica gel.

The amount of the cellulose derivative supported on the silica gel was about 18% (calculated by supposing that the cellulose derivative, in which 2.5 hydroxyl groups, among 3, contained in the glucose unit of cellulose had been carbamoylated, was supported on the silica gel).

COMPARATIVE EXAMPLE 2

(Preparation of separating agent composed of silica gel coated with cellulose tris(3,5-dimethylphenyl-carbamate))

Under a nitrogen atmosphere, 3.5 kg of cellulose (degree of polymerization about 300) was added to 56 l of pyridine. Then, 3,5-dimethylphenyl isocyanate was added thereto in large excess (23.1 kg) of the cellulose at 100° C. The mixture thus obtained was stirred at 105° C. and reacted for 12 hours. Next, the reaction liquid was cooled and 3 l of methanol was added thereto. The obtained mixture was poured into 160 l of methanol. The precipitate thus formed was recovered by filtration and then dried. Thus, 11.8 kg of cellulose tris(3,5-dimethylphenylcarbamate) was obtained (yield 88%).

720 g of the cellulose tris(3,5-dimethylphenyl-carbamate) thus obtained was dissolved in 4.7 l of acetone. The resulting solution was dropped into 2,880 g of 3-aminopropylsilane-treated silica gel (Daiso SP-1000) under stirring. The mixture thus obtained was completely mixed and then the solvent was volatilized. Thus, 3,580 g of a separating agent was obtained.

APPLICATION EXAMPLE 1

The separating agent composed of a polysaccharide derivative immobilized on silica gel prepared in Example 1 was employed as a column packing. It was packed in a stainless steel column having a height 25 cm in height and an inner diameter of 0.46 cm by the slurry packing method to thereby prepare a column for optical resolution.

This column was used as such or after washing with various organic solvents. The optical resolution of various racemic modifications as shown in Table 1 was effected. As the high performance liquid chromatography (HPLC) column, JASCO 875-UV, mfd. by Nippon Bunko, was used. The experiment was conducted at a flow rate of the eluent of 1.0 ml/min and at a temperature of 25° C.

Table 1 shows the results.

The terms given in the table are each defined as follows.

$$\text{Capacity factor } (k_1') = \frac{\text{(retention time of antipode)} - \text{(dead time)}}{\text{(dead time)}}$$

$$\text{Separation factor } (\alpha) = \frac{\text{capacity factor of antipode adsorbed more strongly}}{\text{capacity factor of antipode adsorbed more weakly}}$$

$$\text{Resolution } (Rs) = \frac{2 \times \left( \begin{array}{c} \text{distance between peak of antipode} \\ \text{adsorbed more strongly and peak} \\ \text{of antipode adsorbed more weakly} \end{array} \right)}{\text{sum of band widths of both peaks}}$$

APPLICATION EXAMPLE 2

The separating agent prepared in Comparative Example 1 was used as a column packing and packed into a stainless column having a height of 10 cm and an inner diameter of 0.46 cm by the slurry packing method to thereby prepare a column.

After the column thus obtained was washed with various organic solvents, the optical resolution of various racemic modifications as shown in Table 1 was effected with the use of the column. As the high performance liquid chromatography (HPLC) column, JASCO 875-UV, mfd. by Nippon Bunko, was used. The experiment was conducted at a flow rate of the eluent of 0.4 ml/min and at a temperature of 25° C.

Table 1 shows the results.

TABLE 1

| Racemic compd. | Column of Ex. 1 just after preparation[1] | | | Column of Ex. 1 after washing[2] | | | Column of Comp. Ex. 1 after washing[3] | | |
|---|---|---|---|---|---|---|---|---|---|
| | $k_1'$ | α | Rs | $k_1'$ | α | Rs | $k_1'$ | α | Rs |
| CF₃—CH(OH)—anthracenyl | 1.40 | 2.19 | 7.83 | 1.31 | 2.06 | 6.86 | 1.99 | 1.55 | 2.85 |
| 3-phenyl-chroman-4-one | 1.01 | 1.15 | 1.27 | 0.99 | 1.13 | 1.14 | 1.37 | not resolved | |
| 2-phenylcyclohexanone | 0.81 | 1.25 | 1.90 | 0.81 | 1.25 | 1.87 | 1.00 | 1.14 | 0.71 |
| Ph—C(O)—CH(OH)—Ph (benzoin) | 1.84 | 1.17 | 1.73 | 1.82 | 1.16 | 1.63 | 2.57 | not resolved | |
| bis-tolyl diamine (N,N compound) | 0.60 | 1.53 | 2.85 | 0.57 | 1.61 | 3.21 | 1.06 | 1.30 | 1.29 |

Note)
[1] The column prepared in Example 1 Eluent: hexane/isopropanol = 9/1 (v/v)
[2] The one obtained by washing the column prepared in Example 1 with THF, acetone and methanol at a flow rate of 1.0 ml/min for 30 minutes each Eluent: hexane/isopropanol = 9/1 (v/v)
[3] The one obtained by washing the column prepared in Comparative Example 1 with THF and acetone each at a flow rate of 1.0 ml/min for 30 minutes Eluent: hexane/isopropanol = 9/1 (v/v)

APPLICATION EXAMPLE 3

The separating agent prepared in Comparative Example 2 was used as a column packing and packed into stainless columns each having a height of 25 cm and an inner diameter of 0.46 cm by the slurry packing method to thereby prepare 2 columns for optical resolution.

One column as such was subjected to the experiment for optical resolution of various racemic modifications as shown in Table 2 and thus, the results as given in Table 2 were obtained. The experiment was conducted under conditions that the eluent was a mixture of hexane with isopropanol (9/1 (v/v)), the flow rate of the eluent was 1.0 ml/min and the temperature was 25° C.

Another column was washed successively with 4 mixtures of hexane/isopropanol/tetrahydrofuran (mixing ratio (volume ratio)=9/1/1, 9/1/2, 9/1/4 and 9/1/8) and methanol for 30 minutes for and then subjected to the experiment for optical resolution of various racemic modifications as shown in Table 2. Thus, the results as given in Table 2 were obtained. The experiment was conducted under conditions that the eluent was a mixture of hexane with isopropanol (9/1 (v/v)), the flow rate of the eluent was 1.0 ml/min and the temperature was 25° C.

TABLE 2

| Racemic compd. | Column of Comp. Ex. 2 before washing | | | Column of Comp. Ex. 2 after washing | | |
| --- | --- | --- | --- | --- | --- | --- |
| | $k_1'$ | $\alpha$ | Rs | $k_1'$ | $\alpha$ | Rs |
| 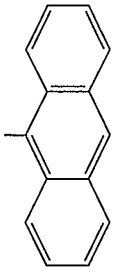 | 1.75 | 3.55 | 13.01 | 1.09 | 3.04 | 2.93 |
| 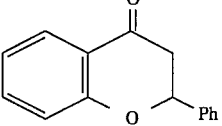 | 1.38 | 1.48 | 3.62 | 0.79 | 1.40 | 1.03 |
| 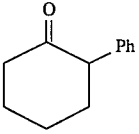 | 1.20 | 1.13 | 1.08 | 0.78 | not resolved | |
| 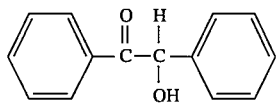 | 2.28 | 1.65 | 6.36 | 1.34 | 1.57 | 1.62 |

We claim:

1. A separating agent for optical isomers comprising a polysaccharide derivative immobilized on a support, the molecules of the polysaccharide derivative being solely crosslinked with each other through a crosslinking reaction and at least the surface of the support being inactive to said crosslinking reaction.

2. The separating agent for optical isomers as set forth in claim 1 wherein the support is a surface-inactivated silica gel having a particle size of from 1 μm to 10 mm and a pore size of from 10 to 100 μm.

3. The separating agent for optical isomers as set forth in claim 1 wherein the polysaccharide derivative before the crosslinkage is an ester or a carbamate derivative of cellulose or amylose having at least 0.1 unreacted hydroxyl group per glucose unit.

4. The separating agent for optical isomers as set forth in claim 1 wherein the polysaccharide derivative before the crosslinkage is an ester or a carbamate derivative of cellulose or amylose having at least 0.1 reactive functional group per glucose unit introduced into the cellulose or the amylose so as to convert it into the ester or carbamate derivative thereof.

5. The separating agent for optical isomers as set forth in claim 1 which is used in chromatography.

6. The separating agent for optical isomers as set forth in claim 1, wherein the support is made of an inert material.

7. The separating agent for optical isomers as set forth in claim 1, wherein the polysaccharide derivative has a crosslinking ratio of from 1 to 20%.

8. A process for producing a separating agent for optical isomers comprising the steps of providing a polysaccharide derivative on a support and crosslinking the molecules of the polysaccharide derivative solely with each other through a crosslinking reaction in the presence of a polyfunctional crosslinking agent to immobilize the polysaccharide derivative on the support, said support having at least its surface inactive to the crosslinking reaction.

9. The process for producing a separating agent for optical isomers as set forth in claim 8, wherein the support is made of an inert material.

10. The process for producing a separating agent for optical isomers as set forth in claim 8, wherein the support is a silica gel.

11. The process for producing a separating agent for optical isomers as set forth in claim 8, wherein the polysaccharide derivative has a crosslinking ratio of from 1 to 20%.

12. The process for producing a separating agent for optical isomers as set forth in claim 8 wherein the polysaccharide derivative before the crosslinkage is an ester or a carbamate derivative of cellulose or amylose having at least 0.1 unreacted hydroxyl group per glucose unit.

13. The process for producing a separating agent for optical isomers as set forth in claim 5 wherein the polysaccharide derivative before the crosslinkage is an ester or a carbamate derivative of cellulose or amylose having at least 0.1 reactive functional group per glucose unit introduced into the cellulose or the amylose so as to convert it into the ester or carbamate derivative thereof.

14. The process for producing a separating agent for optical isomers as set forth in claim 8 wherein said polyfunctional crosslinking agent is a diisocyanate derivative, an acid chloride derivative of a dicarboxylic acid, a diepoxy derivative or a divinyl derivative.

15. The process for producing a separating agent for optical isomers as set forth in claim 8 wherein the polysaccharide is cellulose or amylose and the hydroxyl groups at the 6-position of cellulose or amylose are selectively crosslinked with each other.

16. A process for separating a mixture of optical isomers comprising the step of contacting the mixture with a separating agent comprising a polysaccharide derivative immobilized on a support, the molecules of the polysaccharide derivative being solely crosslinked with each other through a crosslinking reaction and at least the surface of the support being inactive to said crosslinking reaction, to separate the mixture of optical isomers from each other.

17. The process for separating a mixture of optical isomers according to claim 16, wherein the support is made of an inert material.

18. The process for separating a mixture of optical isomers according to claim 16, wherein the support is a silica gel.

19. The process for separating a mixture of optical isomers according to claim 16, wherein the polysaccharide derivative has a crosslinking ratio of from 1 to 20%.

* * * * *

UNITED STATES PATENT AND TRADEMARK OFFICE
CERTIFICATE OF CORRECTION

PATENT NO. : 5 587 467
DATED : December 24, 1996
INVENTOR(S) : Tatsushi MURAKAMI et al It is certified that error appears in the above-indentified patent and that said Letters Patent is hereby corrected as shown below:

Column 14, line 55; change "claim 5" to ---claim 8---.

Signed and Sealed this

Twelfth Day of August, 1997

Attest:

BRUCE LEHMAN

*Attesting Officer*   *Commissioner of Patents and Trademarks*